(12) United States Patent
Karube et al.

(10) Patent No.: US 8,816,140 B2
(45) Date of Patent: Aug. 26, 2014

(54) PROCESS FOR PRODUCING FLUORINE-CONTAINING ALKENE COMPOUND

(75) Inventors: Daisuke Karube, Settsu (JP); Yuzo Komatsu, Settsu (JP); Atsushi Suzuki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/574,921

(22) PCT Filed: Feb. 8, 2011

(86) PCT No.: PCT/JP2011/053062
§ 371 (c)(1),
(2), (4) Date: Jul. 24, 2012

(87) PCT Pub. No.: WO2011/099605
PCT Pub. Date: Aug. 18, 2011

(65) Prior Publication Data
US 2012/0330073 A1 Dec. 27, 2012

Related U.S. Application Data

(60) Provisional application No. 61/282,430, filed on Feb. 12, 2010.

(51) Int. Cl.
*C07C 17/25* (2006.01)
*C07C 17/07* (2006.01)
*C07C 17/087* (2006.01)

(52) U.S. Cl.
USPC .......... 570/156; 570/164; 570/169; 570/220; 570/227; 570/248

(58) Field of Classification Search
None
See application file for complete search history.

(56) References Cited

U.S. PATENT DOCUMENTS

2007/0197842 A1* 8/2007 Mukhopadhyay et al. ... 570/155
2009/0182179 A1 7/2009 Merkel et al.
(Continued)

FOREIGN PATENT DOCUMENTS

EP 2 103 587 9/2009
WO 2008/040969 4/2008
(Continued)

OTHER PUBLICATIONS

International Search Report issued Nov. 17, 2011 in International (PCT) Application No. PCT/JP2011/053062.
(Continued)

*Primary Examiner* — Fereydoun G Sajjadi
*Assistant Examiner* — Medhanit Bahta
(74) *Attorney, Agent, or Firm* — Wenderoth, Lind & Ponack, L.L.P.

(57) ABSTRACT

The present invention provides a process for producing a fluorine-containing alkene of the general formula $CF_3(CX_2)_nCF=CH_2$, wherein X each independently represents F or Cl, and n is an integer of 0 to 2. The process includes a first reaction step of allowing a specific chlorine-containing compound to react with a fluorinating agent under increased pressure in a gas phase in the presence of at least one fluorination catalyst selected from the group consisting of chromium oxide and fluorinated chromium oxide, and a second reaction step of heating the product of the first reaction step in a gas phase under a pressure lower than the pressure in the first reaction step. The process of the present invention can produce a fluorine-containing alkene with a high selectivity with the use of a catalyst that can be easily handled, while suppressing production of by-products that cannot be easily converted into the target or separated.

8 Claims, 1 Drawing Sheet

(56) References Cited

U.S. PATENT DOCUMENTS

2009/0203945 A1    8/2009  Mukhopadhyay et al.
2010/0036179 A1*  2/2010  Merkel et al. ................ 570/156

FOREIGN PATENT DOCUMENTS

| WO | 2008/054781 | 5/2008 |
| WO | 2009/003084 | 12/2008 |
| WO | 2009/125199 | 10/2009 |
| WO | 2009/125200 | 10/2009 |
| WO | 2009/137658 | 11/2009 |
| WO | 2009/158321 | 12/2009 |

OTHER PUBLICATIONS

Written Opinion of the International Searching Authority issued Nov. 17, 2011 in International (PCT) Application No. PCT/JP2011/053062, of which the present application is the national stage.

* cited by examiner

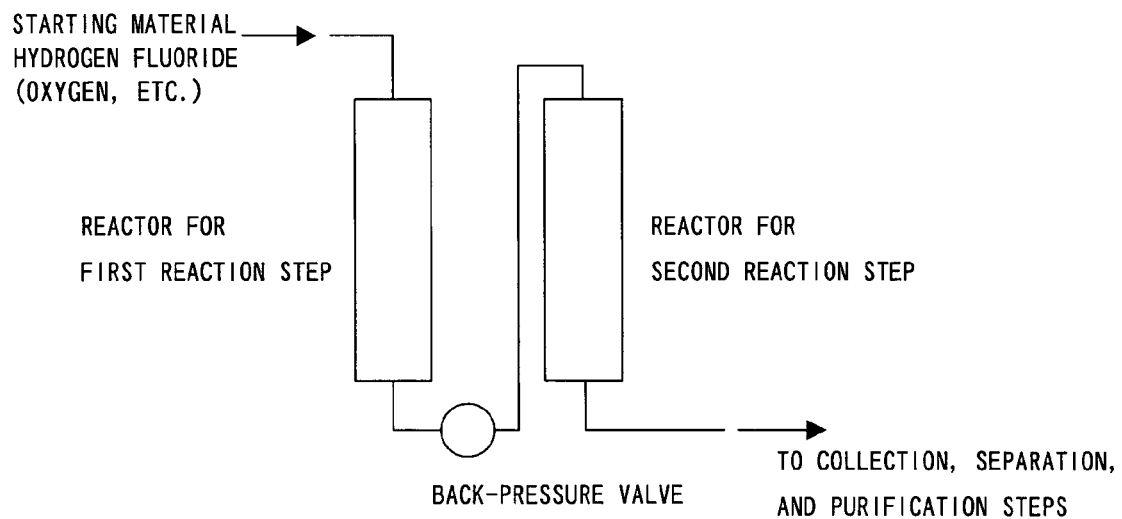

PROCESS FOR PRODUCING FLUORINE-CONTAINING ALKENE COMPOUND

This application claims the benefit of U.S. provisional application No. 61/282,430, filed on Feb. 12, 2010, the contents of which are incorporated by reference.

TECHNICAL FIELD

The present invention relates to a process for producing a fluorine-containing alkene compound.

BACKGROUND ART

Fluorine-containing alkenes with the terminal —CF=$CH_2$ group are useful compounds as various functional materials, solvents, refrigerants, and blowing agents. Fluorine-containing alkenes are also used as the monomers of functional polymers, or starting materials of such monomers, for example, monomers for modifying an ethylene-tetrafluoroethylene copolymer. Further, the compound of the chemical formula $CF_3CF$=$CH_2$ (HFO-1234yf) has recently gained attention as it offers promising prospects as a refrigerant compound of low global warming potential.

As a process for producing fluorine-containing alkenes with the terminal —CF=$CH_2$ group, a method is known in which the starting material chlorine-containing alkane or chlorine-containing alkene with the same number of carbon atoms as that of the target fluorine-containing alkene is converted into a fluorine-containing alkene by reaction with a fluorinating agent using a catalyst. For example, many methods have been reported in which a starting material compound is reacted with anhydrous hydrogen fluoride used as a fluorinating agent in a gas phase in the presence of a fluorination catalyst that includes chromium oxide or fluorinated chromium oxide.

However, as a rule, the methods using chromium oxide or fluorinated chromium oxide inevitably produce certain amounts of plural by-products that cannot be converted into the target, causing problems such as reduction in the yield of the target fluorine-containing terminal alkene, and complications in the purification step. The latter is particularly problematic because the fluorine-containing alkene containing the same number of carbon atoms as the target, and having the terminal —CF=CHW group (W is F or Cl) has a boiling point close to that of the target. Generally, by-product production increases as the conversion of the starting material is increased by, for example, raising the reaction temperature.

Further, it is often the case in the foregoing methods that the starting material or intermediates that can be converted into the target remain at the reactor outlet. Though recycling of these starting material and intermediates in the repeated step of collecting the materials from the reactor outlet and feeding it back to the reactor inlet is possible for more efficient use, nonreusable by-products are concentrated during the production and hinder the producing process.

Methods are proposed in which the target is obtained by a fluorination reaction with anhydrous hydrogen fluoride in a gas phase or liquid phase in the presence of an antimony catalyst such as antimony chloride, followed by dehydrohalogenation (see, for example, Patent Literatures 1 and 2). While these methods are relatively effective at suppressing the production of by-product compounds, there is a problem of handling because the antimony chloride is sensitive to moisture and oxygen, and is easily deactivated. Further, the antimony catalyst cannot be used for extended time periods even in the absence of contact with moisture or oxygen, and a complicated reactivating process using a chlorine gas or the like is required.

Even with the reactivating process, difficulties remain in stably using the antimony catalyst for extended time periods, because antimony chloride or fluorinated antimony fluoride has a low boiling point and a low melting point, and the antimony catalyst flows out from the fixed layer of the catalyst when used in a gas phase. Further, because antimony chloride is highly corrosive to materials such as metal, use of expensive materials is necessary to prevent corrosion particularly in a liquid phase reaction.

The chromium oxide catalyst or fluorinated chromium oxide catalyst is less problematic than the antimony catalyst, because these catalysts are more stable and less corrosive, and are therefore easier to handle in industrial use. However, the conversion of the starting material is considerably poor in the reaction conditions described in, for example, Patent Literature 1 (for example, under the preferred temperature condition of about 30 to 200° C.), and the target fluorine-containing alkene cannot be obtained with high efficiency.

Patent Literature 3 describes a method intended to improve the conversion of the starting material by raising the reaction pressure in a system using a chromium oxide catalyst. However, the product produced by this method contains not only the target fluorine-containing alkene, but large amounts of fluorine-containing alkane that results from the addition of hydrogen fluoride to the fluorine-containing alkene. The fluorine-containing alkane can be thought as an intermediate of the target fluorine-containing alkene, and Patent Literature 3 describes reusing the intermediate or starting material by returning it to the reactor. However, these materials cannot be efficiently converted into the target fluorine-containing alkene, even when circulated in the reactor under the reaction conditions described in this publication.

CITATION LIST

Patent Literature

PTL 1: US2009182179
PTL 2: US2009203945
PTL 3: WO2009/003084

SUMMARY OF INVENTION

Technical Problem

The present invention has been made under these circumstances, and a primary object of the invention is to provide a process for producing a fluorine-containing alkene with a high selectivity with the use of a catalyst that can be easily handled, while suppressing production of by-products that cannot easily be converted into the target or separated.

Solution to Problem

The present inventors conducted intensive studies to achieve the foregoing object, and devised a process that uses a specific chlorine-containing alkene or chlorine-containing alkane as the starting material, and that includes a first reaction step of converting the starting material into a fluorine-containing alkane by a fluorination reaction performed under increased pressure in the presence of a chromium oxide catalyst or a fluorinated chromium oxide catalyst, and a second reaction step of subjecting the fluorine-containing alkane to a dehydrohalogenation reaction under the pressure lower than the reaction pressure in the first step. The process was found to be capable of efficiently producing a fluorine-containing alkene with a greatly improved selectivity for the fluorine-containing alkene and for the intermediate that can be converted into the fluorine-containing alkene, while suppressing production of by-products that cannot easily be converted into the target fluorine-containing alkene or separated. The present invention was completed based on this finding upon further studies.

Specifically, the present invention provides a fluorine-containing alkene producing process, as follows.

1. A process for producing a fluorine-containing alkene represented by the general formula (1):

$$CF_3(CX_2)_nCF\!=\!CH_2,$$

wherein X each independently represents F or Cl, and n is an integer of 0 to 2, provided that n is 0 when a chlorine-containing alkene represented by the general formula (4) below is used as a chlorine-containing compound, the process comprising:

(i) a first reaction step of allowing at least one chlorine-containing compound selected from the group consisting of a chlorine-containing alkane represented by the general formula (2): $CX_3(CX_2)_nCClYCH_2Z$, wherein X each independently represents F or Cl, Y is H or F, Z is Cl or F when Y is H, and Z is H when Y is F, and n is an integer of 0 to 2; a chlorine-containing alkene represented by the general formula (3): $CX_3(CX_2)_nCCl\!=\!CH_2$, wherein X each independently represents F or Cl, and n is an integer of 0 to 2; and a chlorine-containing alkene represented by the general formula (4): $CH_2XCCl\!=\!CX_2$, wherein X each independently represents F or Cl, to react with a fluorinating agent under increased pressure in a gas phase in the presence of at least one fluorination catalyst selected from the group consisting of chromium oxide and fluorinated chromium oxide; and (ii) a second reaction step of heating the product of the first reaction step in a gas phase under a pressure lower than the pressure in the first reaction step to perform a dehydrohalogenation reaction of a fluorine-containing alkane that is contained in the product of the first reaction step, and that is represented by the general formula (5): $CF_3(CX_2)_nCFACH_3$, wherein X each independently represents F or Cl, A is F or Cl, and n is an integer of 0 to 2, provided that n is 0 when a chlorine-containing alkene represented by the general formula (4) is used as the chlorine-containing compound.

2. The process according to Item 1, wherein the fluorinating agent used in the first reaction step is anhydrous hydrogen fluoride.

3. The process according to Item 1 or 2, wherein the fluorination catalyst used in the first reaction step is at least one catalyst selected from the group consisting of chromium oxide of the composition formula: $CrO_m$ (1.5<m<3), and fluorinated chromium oxide obtained by fluorination of the chromium oxide.

4. The process according to any one of Items 1 to 3, wherein the pressure in the first reaction step ranges from 0.3 MPa to 5 MPa.

5. The process according to any one of Items 1 to 4, wherein the chlorine-containing compound used in the first reaction step is at least one compound selected from the group consisting of a chlorine-containing alkane of the general formula (2) with n=0; a chlorine-containing alkene represented by the general formula (3) with n=0; and a chlorine-containing alkene represented by the general formula (4).

6. The process according to any one of Items 1 to 5, wherein the chlorine-containing compound used in the first reaction step is at least one compound selected from the group consisting of $CCl_3CHClCH_2Cl$, $CF_3CFClCH_3$, $CCl_3CCl\!=\!CH_2$, $CH_2ClCCl\!=\!CCl_2$, and $CF_3CCl\!=\!CH_2$.

7. The process according to any one of Items 1 to 6, wherein the pressure in the second reaction step is lower than the pressure in the first reaction step, and ranges from atmospheric pressure to 0.3 MPa.

8. The process according to any one of Items 1 to 7, wherein the second reaction step is performed in the presence of at least one catalyst selected from the group consisting of chromium oxide represented by the composition formula: $CrO_m$ (1.5<m<3), and fluorinated chromium oxide obtained by fluorination of the chromium oxide.

9. The process according to any one of Items 1 to 8, wherein reaction temperatures in the first reaction step and the second reaction step range from 200 to 550° C.

The process for producing a fluorine-containing alkene of the present invention is a combined, two-step reaction process that includes a first reaction step and a second reaction step. The process enables production of a fluorine-containing alkene of the general formula (1): $CF_3(CX_2)_nCF\!=\!CH_2$, wherein X each independently represents F or Cl, and n is an integer of 0 to 2, provided that n is 0 when a chlorine-containing alkene of the general formula (4) below is used as the chlorine-containing compound, with a high selectivity. The following specifically describes the first reaction step and the second reaction step of the process of the present invention.

(1) First Reaction Step

The first reaction step is the step in which a specific chlorine-containing compound as the starting material is allowed to react with a fluorinating agent under increased pressure in the presence of at least one fluorination catalyst selected from the group consisting of chromium oxide and fluorinated chromium oxide. This step enables the production of the target fluorine-containing alkene of general formula (1), and a fluorine-containing alkane that can be easily converted into the fluorine-containing alkene of general formula (1) in the second reaction step described later, with a high selectivity, while suppressing production of by-products.

Raw Material Compound

In the first reaction step of the present invention, at least one chlorine-containing compound selected from the group consisting of a chlorine-containing alkane of general formula (2), a chlorine-containing alkene of general formula (3), and a chlorine-containing alkene of general formula (4) is used as the starting material. Each of these general formulae is as follows.

(i) General Formula (2): $CX_3(CX_2)_nCClYCH_2Z$

In the general formula (2), X each independently represents F or Cl, Y is H or F, Z is Cl or F when Y is H, and Z is H when Y is F, and n is an integer of 0 to 2.

(ii) General Formula (3): $CX_3(CX_2)_nCCl\!=\!CH_2$

In the general formula (3), X each independently represents F or Cl, and n is an integer of 0 to 2.

(iii) General Formula (4): $CH_2XCCl\!=\!CX_2$

In the general formula (4), X each independently represents F or Cl.

Preferred as the starting material compounds used in the process of the present invention are chlorine-containing compounds with n=0 from among the chlorine-containing alkane of general formula (2) and the chlorine-containing alkene of general formula (3); and the chlorine-containing alkene of general formula (4), because these compounds have appropriate boiling points for the gas phase reaction.

Particularly preferred as the starting material compounds used in the present invention are compounds represented by, for example, $CCl_3CHClCH_2Cl$, $CF_3CFClCH_3$, $CCl_3CCl\!=\!CH_2$, $CH_2ClCCl\!=\!CCl_2$, and $CF_3CCl\!=\!CH_2$ from among the chlorine-containing compounds of general formulae (2) to (4). Of these, a compound of the chemical formula $CF_3CCl=CH_2$ (HCFC-1233xf) is particularly preferred.

HCFC-1233xf is a known compound, and can easily be obtained by, for example, the addition of chlorine to 3,3,3-trifluoro-1-propane, followed by the elimination of HCl with an alkali or the like.

Catalyst

In the first reaction step of the present invention, at least one fluorination catalyst selected from the group consisting of chromium oxide and fluorinated chromium oxide is used as the catalyst.

The chromium oxide is not particularly limited. For example, it is preferable to use chromium oxide represented by the composition formula: $CrO_m$, wherein $1.5<m<3$, more preferably $2<m<2.75$, and even more preferably $2<m<2.3$. Any chromium oxide catalysts in the form of powder, pellets, etc. can be used, as long as they are suitable for the reaction. Particularly, pellet-type catalysts are preferred. The above chromium oxide catalyst can be produced, for example, by the process disclosed in Japanese Unexamined Patent Publication No. 5-146680.

The fluorinated chromium oxide can be produced by the process disclosed in Japanese Unexamined Patent Publication No. 5-146680. For example, it can be obtained by fluorinating the chromium oxide obtained by the above process with hydrogen fluoride (HF treatment). The temperature of fluorination may be, for example, about 100 to 460° C.

Although the surface area of the catalyst is decreased after fluorination treatment, the activity of the catalyst is generally higher with a larger specific surface area. The specific surface area after fluorination treatment is preferably about 25 to 130 $m^2/g$, and more preferably about 40 to 100 $m^2/g$, although not limited thereto. In the present specification, the specific surface area is measured by the BET method.

The fluorination reaction of chromium oxide can alternatively be carried out by supplying hydrogen fluoride to a reactor filled with chromium oxide, prior to the first reaction step. After chromium oxide is fluorinated in this manner, the starting material is supplied to the reactor, thereby efficiently promoting the production reaction of the desired product.

The degree of fluorination of the catalyst is not particularly limited; for example, the fluorine content is preferably about 10 to 30 wt. %.

Further, the chromium-based catalyst disclosed in Japanese Unexamined Patent Publication No. 11-171806 can also be used as a chromium oxide catalyst or a fluorinated chromium oxide catalyst. The chromium-based catalyst is in an amorphous state and comprises, as a main component, a chromium compound containing at least one metal element selected from the group consisting of indium, gallium, cobalt, nickel, zinc, and aluminum. The chromium in the chromium compound has an average valence number of not less than +3.5 and not more than +5.0.

The chromium oxide catalyst or fluorinated chromium oxide catalyst may be used by being supported on a carrier such as alumina and activated carbon.

Reaction Method

In the first reaction step, the starting material chlorine-containing compound is allowed to react with a fluorinating agent in a gas phase under increased pressure, in the presence of at least one fluorination catalyst selected from the group consisting of chromium oxide and fluorinated chromium oxide.

The method is not limited to a specific process. For example, the starting material chlorine-containing compound and the fluorinating agent may be introduced into a tubular flow reactor charged with the catalyst. The flow reactor may be, for example, an adiabatic reactor, or a multitubular reactor heated with a heat-transmitting medium. Preferably, the reactor is made of a material that is resistant to the corrosive action of hydrogen fluoride, such as Hastelloy, Inconel, Monel, or the like.

The fluorinating agent is not particularly limited, and anhydrous hydrogen fluoride is preferably used. The ratio of the fluorinating agent and the starting material chlorine-containing compound introduced into the reactor is not particularly limited. However, the conversion of the starting material tends to decrease when the amount of fluorinating agent is too small. On the other hand, productivity is reduced when the proportion of the fluorinating agent is too large, because the increased amount of fluorinating agent means increased amounts of fluorinating agent to be separated after the reaction. Considering these, for example, the anhydrous hydrogen fluoride as the fluorinating agent is used in an amount of preferably about 5 moles or more, more preferably about 10 to 100 moles per mole of the starting material chlorine-containing compound.

The starting material and the fluorinating agent may be supplied to the reactor either directly or with gases, such as nitrogen, helium, and argon, inert to the starting material and the catalyst. The concentration of the inert gas may be, for example, about 0 to 80 mol % with respect to the combined amount of the chlorine-containing compound, the fluorinating agent, and the inert gas, plus oxygen gas, if added.

The starting material may be supplied to the reactor with oxygen, in order to maintain catalytic activity for extended time periods. The form of oxygen is not particularly limited, and the oxygen may be introduced solely as an oxygen gas or in the form of oxygen-containing air. The concentration of the oxygen gas is, for example, preferably about 0.1 to 50 mol %, more preferably about 0.1 to 30 mol % with respect to the combined amount of the chlorine-containing compound, the fluorinating agent, and the oxygen gas, plus inert gas, if added. In this case, when the amount of the oxygen gas supplied is too small, the effect of adding oxygen weakens; and when the amount of the oxygen gas supplied is too large, oxygen is wasted and productivity is reduced.

In the first reaction step of the present invention, the starting material chlorine-containing compound and the fluorinating agent need to undergo reaction in a gas phase under increased pressure. By the reaction performed under increased pressure, the production of by-products that cannot be converted into the target fluorine-containing alkene can be suppressed. The reaction performed under increased pressure is considered to relatively suppress the reaction pathway that produces by-products in which the hydrogen atom(s) in the terminal-$CF=CH_2$ group of the target fluorine-containing alkene is replaced with a fluorine atom or a chlorine atom, as compared with a reaction performed under atmospheric pressure.

By-product production can be suppressed by increasing pressure in the first reaction step. However, when the pressure is too high, energy consumption becomes higher, and a high-strength structural member will be required. These are problematic in terms of economy and safety. For this reason, generally, the pressure may be a pressure exceeding atmospheric pressure, for example, about 0.15 MPa to about 10 MPa, particularly preferably about 0.3 MPa to about 5 MPa in terms of an absolute pressure.

The reaction temperature is not particularly limited, and is preferably about 200 to 550° C., more preferably about 250° C. to 450° C. Temperatures above these ranges are not preferable, because such excessive temperatures may increase production of by-product impurities, or may lead to reduced activity as a result of catalyst degradation. Temperatures below these ranges are not preferable either, because it lowers the conversion of the starting material.

The reaction time in the first reaction step is not particularly limited, and may be generally about 0.1 to 100 g·sec/cc, preferably about 5 to 50 g·sec/cc, in terms of a contact time represented by the ratio $W/F_0$ of the catalyst amount W (g) to the total flow rate $F_0$ of the starting material gas flown in the reaction system (flow rate at 0° C. and at 0.1 MPa: cc/sec). Note that the total flow rate of the starting material gas is the combined flow rate of the starting material chlorine-containing compound and the fluorinating agent plus the flow rate of optional components such as inert gas and oxygen.

The first reaction step produces a fluorine-containing alkane of the general formula (5): $CF_3(CX_2)_nCFACH_3$, wherein X each independently represents F or Cl, A is F or Cl, and n is an integer of 0 to 2, provided that n is 0 when a chlorine-containing alkene of general formula (4) is used as the chlorine-containing compound, that can be converted into the fluorine-containing alkene of general formula (1) in the later second reaction step, in addition to the target fluorine-containing alkene of the general formula (1): $CF_3(CX_2)_nCF=CH_2$, wherein X each independently represents F or Cl, and n is an integer of 0 to 2, provided that n is 0 when a chlorine-containing alkene of general formula (4) is used as the chlorine-containing compound, with a high selectivity.

These products can be produced while suppressing the production of by-products that cannot be converted into the fluorine-containing alkene of general formula (1) in the later second reaction step, for example, such as compounds having the terminal —CH=CHW, wherein W is F or Cl, group. Thus, the fluorine-containing alkene of general formula (1) can be produced with a high selectivity by performing the first reaction step and the second reaction step in combination.

(2) Second Reaction Step

The second reaction step in the process of the present invention is the step of heating the product of the first reaction step in a gas phase. In the second reaction step, heating must be performed under a lower pressure than that used in the first reaction step.

In the second reaction step, a fluorine-containing alkane of the general formula (5): $CF_3(CX_2)_nCFACH_3$, wherein X each independently represents F or Cl, A is F or Cl, and n is an integer of 0 to 2, provided that n is 0 when a chlorine-containing alkene of general formula (4) is used as the chlorine-containing compound, contained in the product of the first reaction step undergoes dehydrohalogenation (elimination of HA), and converts into the fluorine-containing alkene of the general formula (1): $CF_3(CX_2)_nCF=CH_2$, wherein X and n are as defined above, with a high selectivity. Further, the residual starting material compound in the product of the first reaction step also undergoes fluorination reaction and dehydrohalogenation reaction, and partly converts into the target fluorine-containing alkene of general formula (1). As a result, the fluorine-containing alkene of general formula (1) can be produced with a high selectivity. Though the product of the first reaction step can be directly used as the starting material for the second reaction step, the product of the first reaction step may be supplied to the second reaction step after removing the HCl or by-products contained in the outlet gas from the first reaction step, in order to further improve the yield or selectivity of the fluorine-containing alkene in the second reaction step.

The reaction pressure in the second reaction step is to be lower than the pressure in the first reaction step. Generally, the pressure in the second reaction step is lower than the pressure in the first step, and ranges from a pressure below atmospheric pressure (0.1 MPa) (for example, about 0.09 MPa in terms of an absolute pressure) to the increased pressure of about 3 MPa, in terms of an absolute pressure. The particularly preferred pressure is from atmospheric pressure (0.1 MPa) to about 0.3 MPa. Most preferably, the reaction is performed under atmospheric pressure (0.1 MPa).

The method of adjusting pressure in the first reaction step and the second reaction step is not particularly limited. For example, the pressure in the first reaction step may be made higher than the pressure in the second reaction step by installing various regulating valves such as a back-pressure value at the outlet of the reactor used in the first step, or by making the diameter of the reactor outlet used in the first step narrower relative to the flow rate, or, alternatively, by installing a barrier.

The second reaction step can be performed in the presence of, or in the absence of, a catalyst. When performed in the presence of a catalyst, the selectivity or yield of the target fluorine-containing alkene can be improved further.

As a catalyst, known catalysts usable in the dehydrohalogenation reaction can be used. Examples thereof include halides and oxides of transition metals, Group 14 and 15 elements, etc. Metal elements in such catalysts have high affinity for a fluorine atom to be removed, and are therefore considered to have an effect of promoting the dehydrofluorination reaction. Specific examples of transition metals include Ti, V, Cr, Mn, Fe, Co, Ni, Cu, Nb, Ta, etc. Specific examples of Group 14 elements include Sn, Pb, etc. Specific examples of Group 15 elements include As, Sb, Bi, etc. Examples of halides of these elements include fluoride, chloride, etc. Among these, examples of preferable catalysts include $SbCl_5$, $SbCl_2$, $SbF_5$, $TaCl_5$, $SnCl_4$, $NbCl_5$, $FeCl_3$, $CrCl_2$, $CrF_2$, $TiCl_4$, $MoCl_5$, $Cr_2O_3$, $CoCl_2$, $NiCl_2$, etc. These catalysts can be used singly or in combination of two or more. Alternatively, they can be supported on a carrier. The carrier to be used is not particularly limited, and examples thereof include porous alumina silicate such as zeolite, aluminum oxide, silicon oxide, activated carbon, titanium oxide, zirconia oxide, zinc oxide, aluminum fluoride, and the like. These can be used singly or in combination thereof, or a structural composite form thereof. Specific examples of catalysts supported on a carrier include $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$, $NiCl_2/AlF_3$, etc.

The particularly preferred catalysts in the present invention include chromium oxide, and fluorinated chromium oxide. Examples of such chromium oxide and fluorinated chromium oxide include crystalline chromium oxide, amorphous chromium oxide, and the like. For example, at least one catalyst selected from the group consisting of chromium oxide and fluorinated chromium oxide used in the first reaction step, particularly at least one catalyst selected from the group consisting of chromium oxide of the composition formula: $CrO_m$ (1.5<m<3), and fluorinated chromium oxide obtained by the fluorination of the chromium oxide can be suitably used.

When the reaction in the second reaction step is performed in the presence of hydrogen fluoride in the manner described below, the fluorination of the catalyst presumably proceeds during the reaction, even when the fluorination treatment is not previously carried out.

The specific reaction method for the second reaction step is not particularly limited, as long as the product of the first reaction step containing the fluorine-containing alkane of the general formula (5): $CF_3(CX_2)_nCFACH_3$, wherein X, A, and n are as defined above, can be sufficiently heated in a gas phase.

In a specific example of an embodiment, a tubular flow reactor may be used with or without a catalyst charged into the reactor, and the outlet gas from the first reaction step reactor may be supplied to the second reaction step reactor either directly or after removing the HCl or by-products contained in the outlet gas.

The reactor used for the second reaction step is not particularly limited, and, as in the first reaction step, a flow reactor, for example, such as an adiabatic reactor, or a multitubular reactor heated with a heat-transmitting medium can be used. Further, it is preferable also in the second reaction step that the reactor be made of a material that is resistant to the corrosive action of hydrogen fluoride, such as Hastelloy, Inconel, Monel, or the like.

The product of the first reaction step introduced to the second reaction step may include gases, such as nitrogen, helium, and argon, inert to the starting material and the catalyst. The concentration of inert gas may be, for example, about 0 to 80 mol % based on the total amount of the gas components introduced to the second reaction step, specifically, the combined amount of the first reaction step product and the inert gas, plus additional components such as oxygen gas and hydrogen fluoride, if added.

Further, when the catalyst is used in the second step, the introduced gas to the reactor may include oxygen to maintain catalytic activity for extended time periods, as in the first reaction step. The form of oxygen is not particularly limited, and the oxygen may be introduced solely as an oxygen gas or in the form of oxygen-containing air. In either case, the oxygen may be supplied in an amount of, for example, about 0.1 to 50 mol % with respect to the total number of moles of the gas components introduced into the second reaction step reactor, specifically, based on the combined amount of the first reaction step product and oxygen gas, plus additional components such as inert gas and hydrogen fluoride, if added.

The gas components introduced to the second reaction step may further include anhydrous hydrogen fluoride. Even when the introduced gas to the second reaction step reactor contains hydrogen fluoride as is the case when anhydrous hydrogen fluoride is used as the fluorinating agent in the first reaction step, the gas supplied to the second reaction step reactor may still contain additional anhydrous hydrogen fluoride. Particularly, when A is F in the general formula (5): $CF_3(CX_2)_nCFACH_3$, wherein X, A, and n are as defined above, representing the fluorine containing alkane contained in the first reaction step product, the selectivity for the fluorine-containing alkene of general formula (1) can greatly improve by the presence of at least 5 moles of anhydrous hydrogen fluoride per mole of the fluorine-containing alkane of general formula (5). In this case, it is particularly preferable that the amount of anhydrous hydrogen fluoride is about 10 to 200 moles per mole of the fluorine-containing alkane of general formula (5).

Generally, the reaction temperature in the second reaction step is preferably about 200° C. to 550° C., more preferably about 300° C. to 450° C. Temperatures far below these ranges are not preferable, because it tends to lower the conversion of the starting material. Temperatures far above these ranges are not preferable either, because such excessive temperatures may increase production of by-product impurities, or may lead to reduced activity as a result of catalyst degradation.

The reaction time is not particularly limited, and, for example, when the catalyst is not used, may be about 1.0 sec to 50 sec in terms of a residence time represented by the ratio $V/F_0$ (sec) of the heated reaction field volume V (cc) to the total flow rate $F_o$ of gas components flown in the reaction field (flow rate at 0° C. and at 0.1 MPa: cc/sec). When the catalyst is used, the reaction time is preferably about 0.1 to 90 g·sec/cc, more preferably about 1 to 50 g·sec/cc in terms of a contact time represented by the ratio $W/F_0$ of the catalyst amount W (g) to the total flow rate $F_0$ of gas components flown in the reaction system (flow rate at 0° C. and at 0.1 MPa: cc/sec). The total flow rate of gas components means the flow rate of the gas component introduced from the first reaction step to the second reaction step plus the flow rate of additional components such as inert gas, oxygen, and hydrogen fluoride optionally added in the second reaction step.

(3) Reaction Product

The fluorine-containing alkene producing process of the present invention including the first reaction step and the second reaction step can produce a fluorine-containing alkene of the general formula (1): $CF_3(CX_2)_nCF=CH_2$, wherein X and n are as defined above, with a high selectivity, using at least one chlorine-containing compound, as a starting material, selected from the group consisting of a chlorine-containing alkane of the general formula (2): $CX_3(CX_2)_nCClYCH_2Z$, wherein X, Y, Z, and n are as defined above; a chlorine-containing alkene of the general formula (3): $CX_3(CX_2)_nCCl=CH_2$, wherein X and n are as defined above; and a chlorine-containing alkene of the general formula (4): $CH_2XCCl=CX_2$, wherein X is as defined above.

The reaction product can be purified and collected by, for example, distillation. The unreacted starting materials or intermediates at the outlet of the second step can be recycled by feeding it back to the first- or second-step reactor after separation and purification. Particularly, the fluorine-containing alkane of the general formula (5): $CF_3(CX_2)_nCFACH_3$, wherein X, A, and n are as defined above, can easily be converted into the target fluorine-containing alkene of general formula (1) by feeding it back to the second reaction step reactor. By recycling the unreacted starting materials in this manner, the process of the present invention can maintain high productivity even when the conversion of the starting material is poor.

Advantageous Effects of Invention

The production process of the present invention can produce a fluorine-containing alkene with a high selectivity from starting materials such as chlorine-containing alkane or chlorine-containing alkene with the use of a catalyst that can be easily handled, while suppressing production of by-products that cannot be easily converted into the target or separated.

BRIEF DESCRIPTION OF DRAWINGS

FIG. 1 is a flow diagram representing an example of a production process of the present invention.

DESCRIPTION OF EMBODIMENTS

The present invention will be described below in more detail with reference to Examples.

Example 1

The first reaction step and the second reaction step were performed according to the flow diagram of FIG. 1, as follows.

First Reaction Step A catalyst (20 g; fluorine content: about 15.0 wt. %) obtained by fluorinating chrome oxide represented by the composition formula: $CrO_2$ was placed in a tubular Hastelloy reactor equipped with a back-pressure valve at its outlet, and having an inner diameter of 15 mm and a length of 1 m. This reactor of the first reaction step was maintained at atmospheric pressure (0.1 MPa) at 365° C. An anhydrous hydrogen fluoride gas and an oxygen gas were supplied to the reactor at 210 cc/min (the flow rate at 0° C. and 0.1 MPa; the same applies hereinafter) and 4 cc/min, respectively, for one hour.

Thereafter, a $CF_3CCl=CH_2$ (HCFC-1233xf) gas was supplied at a flow rate of 21 cc/min, and, immediately, the back-pressure valve was manipulated to change the reactor pressure to 0.3 MPa. The outlet gas from the reactor after 1 hour was analyzed by gas chromatography.

Second Reaction Step

A catalyst (20 g; fluorine content: about 15.0 wt. %) obtained by fluorinating chrome oxide represented by the composition formula: $CrO_2$ was placed in a tubular Hastelloy reactor having an inner diameter of 15 mm and a length of 1 m. This reactor of the second reaction step was maintained at atmospheric pressure (0.1 MPa) at 365° C., and the outlet gas from the first reaction step was introduced into the reactor at a flow rate of 235 cc/min. The outflow form the reactor after 1 hour was analyzed by gas chromatography. Table 1 below shows the analysis results for the first reaction step and the second reaction step.

Example 2

First Reaction Step

The reaction was carried out under the same conditions as in Example 1, except that the pressure in the reactor was changed to 0.6 MPa.

Second Reaction Step

The reaction was carried out under the same conditions as in Example 1, except that the introduced gas was changed to the outlet gas (flow rate of 235 cc/min) from the first reaction step of Example 2.

Table 1 below shows the analysis results for the first reaction step and the second reaction step.

Comparative Example 1

The reaction was carried out under the same conditions as in Example 1, except that the catalyst amount was doubled (40.0 g) and that the pressure was changed to atmospheric pressure (0.1 MPa) in the first reaction step. In this experiment, a single step reaction was performed under atmospheric pressure with a contact time of the catalyst and the introduced gas being matched to the total contact time of the first reaction step and the second reaction step of Example 1.

Table 1 below represents the analysis results of the outlet gas.

The chemical formula of each compound is as follows.

$CF_3CCl=CH_2$ (HCFC-1233xf)

$CF_3CF=CH_2$ (HFC-1234yf)

$CF_3CF_2CH_3$ (HFC-245cb)

$CF_3CH=CHF$ (HFC-1234ze)

$CF_3CH=CHCl$ (HCFC-1233zd)

TABLE 1

|  | Ex. 1 | Ex. 2 | Com. Ex. 1 |
|---|---|---|---|
| First reaction step |  |  |  |
| Pressure (MPa, absolute pressure) | 0.3 | 0.6 | 0.1 (atmospheric pressure) |
| Reaction temperature (° C.) | 365 | 365 | 365 |
| Contact time $W/F_0$ (g · sec/cc) | 5 | 5 | 10 |
| HCFC-1233xf conversion (GC %) | 12.5 | 12.6 | — |
| HFC-1234yf selectivity (GC %) | 52.8 | 23.7 | — |
| HFC-245cb selectivity (GC %) | 39.3 | 74.9 | — |
| HFC-1234ze selectivity (GC %) | 2.9 | 0.1 | — |
| HCFC-1233zd selectivity (GC %) | 1.1 | 0.1 | — |
| Other by-product selectivity (GC %) | 3.9 | 1.2 | — |
| Second reaction step |  |  | — |
| Pressure (MPa, absolute pressure) | 0.1 (atmospheric pressure) | 0.1 (atmospheric pressure) | — |
| Reaction temperature (° C.) | 365 | 365 | — |
| Contact time $W/F_0$ (g · sec/cc) | 5 | 5 | — |
| HCFC-1233xf conversion (GC %) | 21.1 | 21.2 | 16.4 |
| HFC-1234yf selectivity (GC %) | 74.9 | 77.9 | 74.5 |
| HFC-245cb selectivity (GC %) | 15.4 | 15.9 | 14.3 |
| HFC-1234ze selectivity (GC %) | 4.2 | 2.6 | 4.6 |
| HCFC-1233zd selectivity (GC %) | 1.8 | 1.2 | 2.9 |
| Other by-product selectivity (GC %) | 3.7 | 2.4 | 3.7 |
| 1234yf + 245cb selectivity (GC %) | 90.3 | 93.8 | 88.8 |
| Impurities/1234yf (GC % ratio (%)) | 12.9 | 8.0 | 15.0 |

As is clear from these results, selectivity for the target HFC-1234yf improved in Examples 1 and 2 in which the fluorination reaction (first reaction step) was performed under increased pressure followed by the dehydrofluorination reaction (second reaction step) performed under atmospheric pressure, as compared with Comparative Example 1 in which reaction was performed only under atmospheric pressure with the same contact time as the respective total contact times of Examples 1 and 2. The total selectivity including HFC-245cb that can easily convert into HFC-1234yf (i.e., HFC-1234yf+HFC-245cb selectivity) was particularly higher in Examples 1 and 2 than in Comparative Example 1, demonstrating that the proportion of impurities was considerably smaller in Examples 1 and 2.

These results show that the process of the present invention enables efficient production of fluorine-containing alkenes.

Reference Example 1

A catalyst (9.35 g; fluorine content: about 15.0 wt. %) obtained by fluorinating the chromium oxide used in Example 1 was placed in a tubular Hastelloy reactor equipped with a back-pressure valve at its outlet, and having an inner diameter of 15 mm and a length of 1 m. The reactor was maintained at atmospheric pressure (0.1 MPa) at 365° C. An anhydrous hydrogen fluoride (HF) gas and an oxygen gas were supplied to the reactor at 28 cc/min and 0.11 cc/min, respectively, for one hour. This was followed by the supply of $CF_3CF_2CH_3$ (HFC-245cb) at a flow rate of 0.25 cc/min. The HF:HFC-245cb molar ratio was 110:1. The outlet gas of the reactor after 6 hours was analyzed by gas chromatography. The conversion of HFC-245cb was 82%, and the selectivity for HFC-1234yf was 90%.

In contrast, the conversion of HFC-245cb was 74%, and the selectivity for HFC-1234yf was 79% in a reaction performed in the same manner without supplying the anhydrous hydrogen fluoride gas.

These results show that selectivity for the fluorine-containing alkene can be improved by performing the dehydrofluorination reaction in the presence of large amounts of anhydrous hydrogen fluoride in the second reaction step of the present invention.

The invention claimed is:

1. A process for producing a fluorine-containing alkene represented by formula (1):

$$CF_3(CX_2)_nCF=CH_2, \qquad (1)$$

wherein:
X each independently represents F or Cl, and n is an integer of 0 to 2, provided that n is 0 when a chlorine-containing alkene represented by formula (4) (below) is used as a chlorine-containing compound, the process comprising:
(i) a first reaction step of reacting:
at least one chlorine-containing compound selected from the group consisting of:
a chlorine-containing alkane represented by formula (2):

$$CX_3(CX_2)_nCClYCH_2Z, \qquad (2)$$

wherein X each independently represents F or Cl, Y is H or F, Z is Cl or F when Y is H, and Z is H when Y is F, and n is an integer of 0 to 2;
a chlorine-containing alkene represented by formula (3):

$$CX_3(CX_2)_nCCl=CH_2, \qquad (3)$$

wherein X each independently represents F or Cl, and n is an integer of 0 to 2; and
a chlorine-containing alkene represented by formula (4):

$$CH_2XCCl=CX_2, \qquad (4)$$

wherein X each independently represents F or Cl,
with a fluorinating agent under increased pressure of from 0.3 MPa to 5 MPa in a gas phase in the presence of at least one fluorination catalyst selected from the group consisting of chromium oxide and fluorinated chromium oxide, to obtain a product; and
(ii) a second reaction step of heating the product obtained in the first reaction step in a gas phase under a pressure lower than the pressure in the first reaction step to perform a dehydrohalogenation reaction of a fluorine-containing alkane that is contained in the product of the first reaction step, wherein the fluorine-containing alkane is represented by formula (5):

$$CF_3(CX_2)_nCFACH_3, \qquad (5)$$

wherein X each independently represents F or Cl, A is F or Cl, and n is an integer of 0 to 2, provided that n is 0 when a chlorine-containing alkene represented by the formula (4) is used as the chlorine-containing compound,
to obtain the fluorine-containing alkene of the formula (1).

2. The process according to claim 1, wherein the fluorinating agent used in the first reaction step is anhydrous hydrogen fluoride.

3. The process according to claim 1, wherein the fluorination catalyst used in the first reaction step is at least one catalyst selected from the group consisting of chromium oxide represented by the composition formula: $CrO_m$ ($1.5<m<3$), and fluorinated chromium oxide obtained by fluorinating the chromium oxide.

4. The process according to claim 1, wherein the chlorine-containing compound used in the first reaction step is at least one compound selected from the group consisting of the chlorine-containing alkane of the formula (2) wherein n is 0; the chlorine-containing alkene represented by the formula (3) wherein n is 0; and the chlorine-containing alkene represented by the formula (4).

5. The process according to claim 1, wherein the chlorine-containing compound used in the first reaction step is at least one compound selected from the group consisting of $CCl_3CHClCH_2Cl$, $CF_3CFClCH_3$, $CCl_3CCl=CH_2$, $CH_2ClCCl=CCl_2$, and $CF_3CCl=CH_2$.

6. The process according to claim 1, wherein the pressure in the second reaction step is lower than the pressure in the first reaction step, and ranges from atmospheric pressure to 0.3 MPa.

7. The process according to claim 1, wherein the second reaction step is performed in the presence of at least one catalyst selected from the group consisting of chromium oxide represented by the composition formula: $CrO_m$ ($1.5<m<3$), and fluorinated chromium oxide obtained by fluorinating the chromium oxide.

8. The process according to claim 1, wherein reaction temperatures in the first reaction step and the second reaction step range from 200 to 550° C.

* * * * *